United States Patent
Vaillancourt (10) Patent No.: US 10,758,170 B2
(45) Date of Patent: Sep. 1, 2020

(54) DIFFUSION IMAGING IN PARKINSON'S DISEASE AND PARKINSONISM

(71) Applicant: UNIVERSITY OF FLORIDA RESEARCH FOUNDATION, INCORPORATED, Gainesville, FL (US)

(72) Inventor: David E. Vaillancourt, Gainesville, FL (US)

(73) Assignee: UNIVERSITY OF FLORIDA RESEARCH FOUNDATION, INCORPORATED, Gainesville, FL (US)

( * ) Notice: Subject to any disclaimer, the term of this patent is extended or adjusted under 35 U.S.C. 154(b) by 0 days.

(21) Appl. No.: 16/500,185

(22) PCT Filed: Mar. 20, 2018

(86) PCT No.: PCT/US2018/023263
§ 371 (c)(1),
(2) Date: Oct. 2, 2019

(87) PCT Pub. No.: WO2018/194778
PCT Pub. Date: Oct. 25, 2018

(65) Prior Publication Data
US 2020/0046281 A1 Feb. 13, 2020

Related U.S. Application Data

(60) Provisional application No. 62/486,580, filed on Apr. 18, 2017.

(51) Int. Cl.
*A61B 5/00* (2006.01)
*A61B 5/055* (2006.01)

(52) U.S. Cl.
CPC ............ *A61B 5/4082* (2013.01); *A61B 5/055* (2013.01); *A61B 5/4848* (2013.01); *A61B 2576/026* (2013.01)

(58) Field of Classification Search
None
See application file for complete search history.

(56) References Cited

U.S. PATENT DOCUMENTS 9,653,002 B2 * 5/2017 Alberts ................. G09B 23/28
2005/0283054 A1 * 12/2005 Reiman .............. G01N 33/5088
600/300

(Continued)

FOREIGN PATENT DOCUMENTS

CN 106050225 A 10/2016

OTHER PUBLICATIONS

Banerjee, Monami, et al. "A method for automated classification of Parkinson's disease diagnosis using an ensemble average propagator template brain map estimated from diffusion MRI." PloS one 11.6 (2016). (Year: 2016).*

(Continued)

*Primary Examiner* — Andrae S Allison
(74) *Attorney, Agent, or Firm* — Alston & Bird LLP (57) ABSTRACT

A treatment efficacy of a treatment for treating a parkinsonian disease is determined. A first set of imaging information/data associated with a dMRI scan of an individual's brain captured at a first time and a second set of imaging information/data associated with a dMRI scan of the individual's brain captured at a second time are received. The individual underwent the treatment for a time period comprising at least part of the time between the first and second times. An expected change between the first and second times is determined based on a natural progression of the parkinsonian disease. The first and second sets of imaging (Continued)

information/data are analyzed to determine a first free-water pattern and a second free-water pattern. Based on the first and second free-water patterns, a disease progression score is determined. Based on the disease progression score and the expected change, a treatment efficacy for treating the individual with the treatment is determined.

20 Claims, 5 Drawing Sheets

(56) References Cited

U.S. PATENT DOCUMENTS

| | | | |
|---|---|---|---|
| 2008/0045510 A1 | 2/2008 | Liang et al. | |
| 2010/0127704 A1 | 5/2010 | Warntjes | |
| 2013/0147477 A1 | 6/2013 | Singh et al. | |
| 2013/0267825 A1* | 10/2013 | Wohlgemuth | A61B 5/055 600/410 |
| 2013/0289385 A1* | 10/2013 | Lozano | A61N 1/36082 600/411 |
| 2014/0180061 A1 | 6/2014 | Warntjes | |
| 2016/0300352 A1* | 10/2016 | Raj | G06K 9/469 |

OTHER PUBLICATIONS

Galban, C. J., et al. "Diffusion MRI in early cancer therapeutic response assessment." NMR in biomedicine 30.3 (2017): e3458. Year: 2017).*

International Searching Authority, International Search Report and Written Opinion for International Application No. PCT/US2018/023263, dated Aug. 3, 2018, (12 pages), Republic of Korea.

Burciu, Roxana G. et al. *Free-Water and BOLD Imaging Changes in Parkinson's Disease Patients Chronically Treated With A MAO-B Inhibitor*, Human Brain Mapping, (2016), pp. 1-10.

Planetta, Peggy J. *Free-Water Imaging in Parkinson's Disease and Atypical Parkinsonism*, BRAIN A Journal of Neurology, (2016), Issue 139, pp. 495-508. DOI: 10.1093/brain/awv361.

Ofori, Edward. *Longitudinal Changes In Free-Water Within The Substantia Nigra of Parkinson 's Disease.* BRAIN A Journal of Neurology, (2015), pp. 1-10. DOI: 10.1093/BRAIN/AWV136.

* cited by examiner

DIFFUSION IMAGING IN PARKINSON'S DISEASE AND PARKINSONISM

CROSS REFERENCE TO RELATED APPLICATIONS

This application is a National Stage Application, filed under 35 U.S.C. § 371, of International Application No. PCT/US2018/023263, filed Mar. 20, 2018, which claims priority to U.S. Application No. 62/486,580, filed Apr. 18, 2017; the contents of both of which are hereby incorporated by reference in their entirety.

FEDERALLY SPONSORED RESEARCH OR DEVELOPMENT

This invention was made with United States Government support under R01 NS075012 & R01 NS052318 awarded by the National Institutes of Health (NIH). The United States Government has certain rights in the invention.

BACKGROUND

Parkinson's disease is a progressive disorder of the nervous system that affects movement. It develops gradually, sometimes starting with a barely noticeable tremor in just one hand. Parkinson's is often diagnosed based on movement and/or motor symptoms, such as a tremor. However, the disease may begin prior to the onset of movement and/or motor symptoms and it can often be difficult to distinguish between forms of Parkinsonism. Treatment of the disease may be more effective if treatment were to begin in the earliest stages of the disease. Additionally, understanding of the earliest stages and the progression of the disease require identification of individuals with the disease or at an increased risk of developing the disease prior to the onset of noticeable movement and/or motor symptoms. Additionally, to develop medications and/or other therapeutic treatments that effectively treat the disease, a technique for measuring disease progression is required. Effective measurements of disease progression will facilitate future clinical trials testing therapies for Parkinson's disease and Parkinsonism.

BRIEF SUMMARY OF SOME EXAMPLE EMBODIMENTS

An example embodiment of the present invention provides one or more progression biomarkers of Parkinson's disease and/or other parkinsonian diseases. For example, in an example embodiment, a progression score for an individual may be determined over a period of time based on one or more biomarkers. In an example embodiment, biomarkers and tools for determining which people are at a greater risk for developing Parkinson's disease and/or other parkinsonian diseases and/or early diagnosis of Parkinson's and/or other parkinsonian diseases are provided. In particular, in various embodiments, these biomarkers may comprise and/or relate to the free-water fraction in one or more areas of an individual's brain. In an example embodiment, the free-water fraction in one or more areas of an individual's brain may be determined based on analysis of one or more instances of imaging information/data corresponding to a diffusion magnetic radiation imaging (dMRI) scan of the individual's brain. In an example embodiment, the one or more instances of imaging information/data corresponding to the dMRI scan of the individual's brain are analyzed using a bi-tensor analysis model and pipeline for normalization and quantifying images.

According to one aspect of the present invention, a method for determining a free-water pattern of an individual is provided. In an example embodiment, the method comprises receiving at a computing entity an instance of imaging information/data associated with a dMRI scan of an individual's brain; and using by the computing entity at least one of (a) a free-water pattern template or (b) 2D or 3D threshold requirements to determine a free-water pattern for one or more areas of the individual's brain based on at least a portion of the instance of imaging information/data. The free-water pattern may be used to determine the individual's parkinsonian state.

According to another aspect of the present invention, a method for determining a treatment efficacy score for treating a parkinsonian disease in an individual is provided. In an example embodiment, the method comprises receiving at a computing entity a first set of imaging information/data associated with a dMRI scan of an individual's brain and associated with a first time; and receiving at the computing entity a second set of imaging information/data associated with a dMRI scan of the individual's brain and associated with a second time. The individual underwent the treatment for a time period, the time period comprising at least a portion of the time between the first time and the second time. The method further comprises determining by the computing entity an expected change between the first time and the second time based on a natural progression of the parkinsonian disease; analyzing by the computing entity at least a portion of the first set of imaging information/data to determine a first free-water pattern; analyzing by the computing entity at least a portion of the second set of imaging information/data to determine a second free-water pattern; based on the first free-water pattern and the second free-water pattern, determining by the computing entity a disease progression score; and based on the disease progression score and the expected change between the first time and the second time, determining a treatment efficacy score for treating the individual with the treatment. In an example embodiment, a treatment plan for the individual is determined based on the treatment efficacy score.

According to still another aspect of the present invention, an apparatus for determining a free-water pattern of an individual is provided. In an example embodiment, the apparatus comprises at least one processor, a communications interface configured for communicating via at least one network, and at least one memory storing computer program code. The at least one memory and the computer program code are configured to, with the processor, cause the apparatus to at least receive an instance of imaging information/data associated with a dMRI scan of an individual's brain; and use at least one of (a) a free-water pattern template or (b) 2D or 3D threshold requirements to determine a free-water pattern for one or more areas of the individual's brain based on at least a portion of the instance of imaging information/data. The free-water pattern may be used to determine the individual's parkinsonian state.

According to yet another aspect of the present invention, an apparatus for determining a treatment efficacy score for treating a parkinsonian disease in an individual is provided. In an example embodiment, the apparatus comprises at least one processor, a communications interface configured for communicating via at least one network, and at least one memory storing computer program code. The at least one memory and the computer program code are configured to, with the processor, cause the apparatus to at least receive a first set of imaging information/data associated with a dMRI scan of an individual's brain and associated with a first time; and receive a second set of imaging information/data associated with a dMRI scan of the individual's brain and associated with a second time. The individual underwent the treatment for a time period, the time period comprising at least a portion of the time between the first time and the second time. The at least one memory and the computer program code are further configured to, with the processor, cause the apparatus to at least determine an expected change between the first time and the second time based on a natural progression of the parkinsonian disease; analyze at least a portion of the first set of imaging information/data to determine a first free-water pattern; analyze at least a portion of the second set of imaging information/data to determine a second free-water pattern; based on the first free-water pattern and the second free-water pattern, determine a disease progression score; and based on the disease progression score and the expected change between the first time and the second time, determine a treatment efficacy for treating the individual with the treatment. In an example embodiment, a treatment plan for the individual is determined based on the treatment efficacy score.

According to another aspect of the present invention, a computer program product for determining a free-water pattern of an individual is provided. In an example embodiment, the computer program product comprises at least one non-transitory computer-readable storage medium having computer-readable program code portions stored therein. The computer-readable program code portions comprise executable portions configured, when executed by a processor of an apparatus, to cause the apparatus to receive an instance of imaging information/data associated with a dMRI scan of an individual's brain; and use at least one of (a) a free-water pattern template or (b) 2D or 3D threshold requirements to determine a free-water pattern for one or more areas of the individual's brain based on at least a portion of the instance of imaging information/data The free-water pattern may be used to determine the individual's parkinsonian state.

According to yet another aspect of the present invention, a computer program product for a treatment efficacy score for treating a parkinsonian disease in an individual is provided. In an example embodiment, the computer program product comprises at least one non-transitory computer-readable storage medium having computer-readable program code portions stored therein. The computer-readable program code portions comprise executable portions are configured, when executed by a processor of an apparatus, to cause the apparatus to receive a first set of imaging information/data associated with a dMRI scan of an individual's brain and associated with a first time; and receive a second set of imaging information/data associated with a dMRI scan of the individual's brain and associated with a second time. The individual underwent a treatment for a time period, the time period comprises at least a portion of the time between the first time and the second time. In an example embodiment, the computer-readable program code portions further comprise executable portions are configured, when executed by a processor of an apparatus, to cause the apparatus to determine an expected change between the first time and the second time based on a natural progression of the parkinsonian disease; analyze at least a portion of the first set of imaging information/data to determine a first free-water pattern; analyze at least a portion of the second set of imaging information/data to determine a second free-water pattern; based on the first free-water pattern and the second free-water pattern, determine a disease progression score; and based on the disease progression score and the expected change between the first time and the second time, determine a treatment efficacy for treating the individual with the treatment.

BRIEF DESCRIPTION OF THE FIGURES

Having thus described the invention in general terms, reference will now be made to the accompanying drawings, which are not necessarily drawn to scale, and wherein:

DETAILED DESCRIPTION OF VARIOUS EMBODIMENTS

Various embodiments of the present invention now will be described more fully hereinafter with reference to the accompanying drawings, in which some, but not all embodiments of the inventions are shown. Indeed, these inventions may be embodied in many different forms and should not be construed as limited to the embodiments set forth herein; rather, these embodiments are provided so that this disclosure will satisfy applicable legal requirements. The term "or" is used herein in both the alternative and conjunctive sense, unless otherwise indicated. The terms "illustrative" and "exemplary" are used to be examples with no indication of quality level. Like numbers refer to like elements throughout.

I. Computer Program Products, Methods, and Computing Entities

Embodiments of the present invention may be implemented in various ways, including as computer program products that comprise articles of manufacture. A computer program product may include a non-transitory computer-readable storage medium storing applications, programs, program modules, scripts, source code, program code, object code, byte code, compiled code, interpreted code, machine code, executable instructions, and/or the like (also referred to herein as executable instructions, instructions for execution, computer program products, program code, and/or similar terms used herein interchangeably). Such non-transitory computer-readable storage media include all computer-readable media (including volatile and non-volatile media).

In one embodiment, a non-volatile computer-readable storage medium may include a floppy disk, flexible disk, hard disk, solid-state storage (SSS) (e.g., a solid state drive (SSD), solid state card (SSC), solid state module (SSM), enterprise flash drive, magnetic tape, or any other non-transitory magnetic medium, and/or the like. A non-volatile computer-readable storage medium may also include a punch card, paper tape, optical mark sheet (or any other physical medium with patterns of holes or other optically recognizable indicia), compact disc read only memory (CD-ROM), compact disc-rewritable (CD-RW), digital versatile disc (DVD), Blu-ray disc (BD), any other non-transitory optical medium, and/or the like. Such a non-volatile computer-readable storage medium may also include read-only memory (ROM), programmable read-only memory (PROM), erasable programmable read-only memory (EPROM), electrically erasable programmable read-only memory (EEPROM), flash memory (e.g., Serial, NAND, NOR, and/or the like), multimedia memory cards (MMC), secure digital (SD) memory cards, SmartMedia cards, CompactFlash (CF) cards, Memory Sticks, and/or the like. Further, a non-volatile computer-readable storage medium may also include conductive-bridging random access memory (CBRAM), phase-change random access memory (PRAM), ferroelectric random-access memory (FeRAM), non-volatile random-access memory (NVRAM), magnetoresistive random-access memory (MRAM), resistive random-access memory (RRAM), Silicon-Oxide-Nitride-Oxide-Silicon memory (SONOS), floating junction gate random access memory (FJG RAM), Millipede memory, racetrack memory, and/or the like.

In one embodiment, a volatile computer-readable storage medium may include random access memory (RAM), dynamic random access memory (DRAM), static random access memory (SRAM), fast page mode dynamic random access memory (FPM DRAM), extended data-out dynamic random access memory (EDO DRAM), synchronous dynamic random access memory (SDRAM), double data rate synchronous dynamic random access memory (DDR SDRAM), double data rate type two synchronous dynamic random access memory (DDR2 SDRAM), double data rate type three synchronous dynamic random access memory (DDR3 SDRAM), Rambus dynamic random access memory (RDRAM), Twin Transistor RAM (TTRAM), Thyristor RAM (T-RAM), Zero-capacitor (Z-RAM), Rambus in-line memory module (RIMM), dual in-line memory module (DIMM), single in-line memory module (SIMM), video random access memory (VRAM), cache memory (including various levels), flash memory, register memory, and/or the like. It will be appreciated that where embodiments are described to use a computer-readable storage medium, other types of computer-readable storage media may be substituted for or used in addition to the computer-readable storage media described above.

As should be appreciated, various embodiments of the present invention may also be implemented as methods, apparatus, systems, computing devices, computing entities, and/or the like. As such, embodiments of the present invention may take the form of an apparatus, system, computing device, computing entity, and/or the like executing instructions stored on a computer-readable storage medium to perform certain steps or operations. Thus, embodiments of the present invention may also take the form of an entirely hardware embodiment, an entirely computer program product embodiment, and/or an embodiment that comprises combination of computer program products and hardware performing certain steps or operations.

Embodiments of the present invention are described below with reference to block diagrams and flowchart illustrations. Thus, it should be understood that each block of the block diagrams and flowchart illustrations may be implemented in the form of a computer program product, an entirely hardware embodiment, a combination of hardware and computer program products, and/or apparatus, systems, computing devices, computing entities, and/or the like carrying out instructions, operations, steps, and similar words used interchangeably (e.g., the executable instructions, instructions for execution, program code, and/or the like) on a computer-readable storage medium for execution. For example, retrieval, loading, and execution of code may be performed sequentially such that one instruction is retrieved, loaded, and executed at a time. In some exemplary embodiments, retrieval, loading, and/or execution may be performed in parallel such that multiple instructions are retrieved, loaded, and/or executed together. Thus, such embodiments can produce specifically-configured machines performing the steps or operations specified in the block diagrams and flowchart illustrations. Accordingly, the block diagrams and flowchart illustrations support various combinations of embodiments for performing the specified instructions, operations, or steps.

II. Exemplary System Architecture

Figure 1:
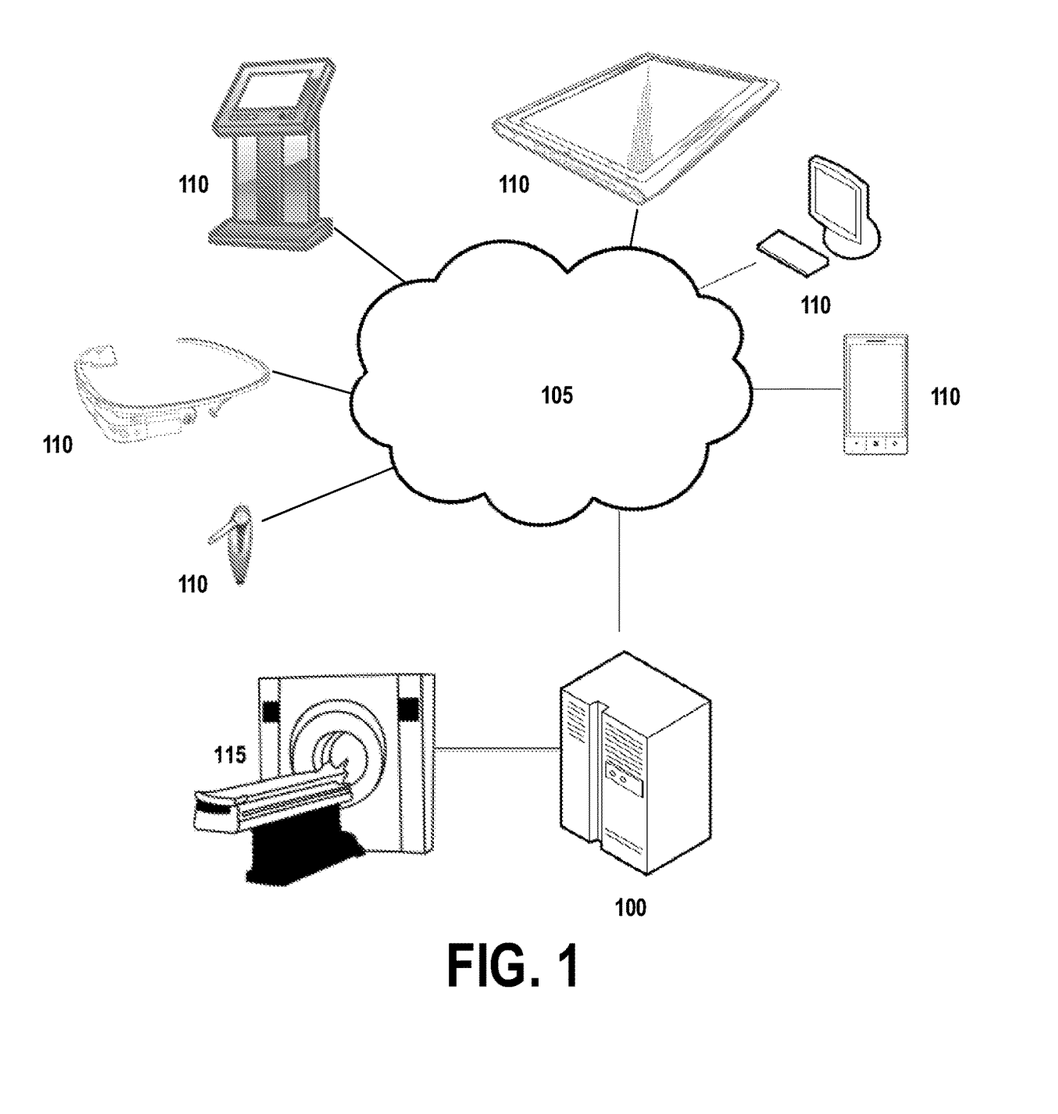
FIG. 1 is an overview of a system that can be used to practice embodiments of the present invention.

FIG. 1 provides an illustration of an exemplary embodiment of the present invention. As shown in FIG. 1, this particular embodiment may include one or more imaging machines 115, one or more assessment computing entities 100, one or more networks 105, and one or more user computing entities 110. Each of these components, entities, devices, systems, and similar words used herein interchangeably may be in direct or indirect communication with, for example, one another over the same or different wired or wireless networks. Additionally, while FIG. 1 illustrates the various system entities as separate, standalone entities, the various embodiments are not limited to this particular architecture.

1. Exemplary Assessment Computing Entity

Figure 2:
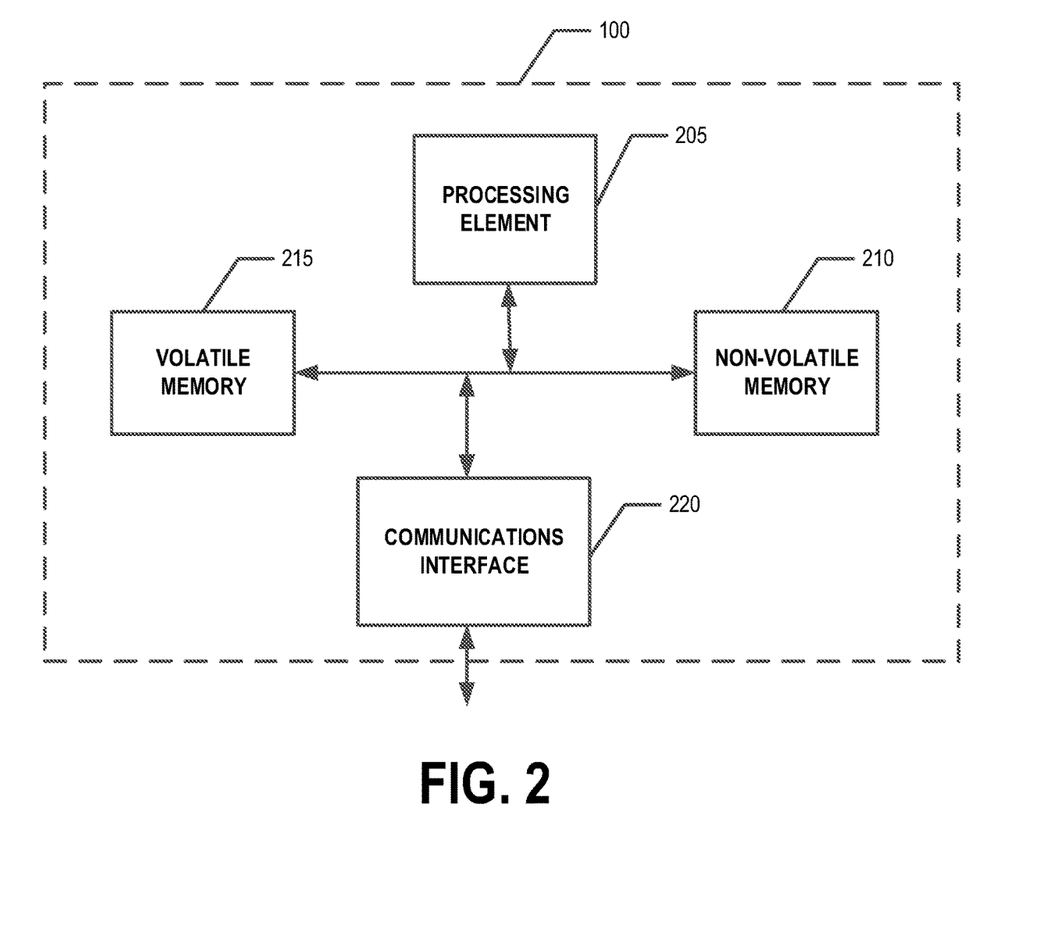
FIG. 2 is an exemplary schematic diagram of an assessment computing entity according to one embodiment of the present invention.

FIG. 2 provides a schematic of an assessment computing entity 100 according to one embodiment of the present invention. An assessment computing entity 100 may belong to, a medical facility, hospital, clinic, diagnostic service, healthcare provider, healthcare provider group, and/or the like. However, the assessment computing entity 100 may belong a third party computing service that performs remote computations for a medical facility. In an example embodiment, an assessment computing entity 100 may be configured to control one or more imaging machines 115 and/or to receive imaging information/data from one or more imaging machines and/or a controller computing entity thereof.

In general, the terms computing entity, computer, entity, device, system, and/or similar words used herein interchangeably may refer to, for example, one or more computers, computing entities, desktop computers, mobile phones, tablets, phablets, notebooks, laptops, distributed systems, input terminals, servers or server networks, blades, gateways, switches, processing devices, processing entities, set-top boxes, relays, routers, network access points, base stations, the like, and/or any combination of devices or entities adapted to perform the functions, operations, and/or processes described herein. Such functions, operations, and/or processes may include, for example, transmitting, receiving, operating on, processing, displaying, storing, determining, creating/generating, monitoring, evaluating, comparing, and/or similar terms used herein interchangeably. In one embodiment, these functions, operations, and/or processes can be performed on data, content, information, and/or similar terms used herein interchangeably.

As indicated, in one embodiment, the assessment computing entity 100 may also include one or more communications interfaces 220 for communicating with various computing entities, such as by communicating data, content, information, and/or similar terms used herein interchangeably that can be transmitted, received, operated on, processed, displayed, stored, and/or the like. For instance, the assessment computing entity 100 may communicate with user computing entities 110 and/or a variety of other computing entities.

As shown in FIG. 2, in one embodiment, the assessment computing entity 100 may include or be in communication with one or more processing elements 205 (also referred to as processors, processing circuitry, and/or similar terms used herein interchangeably) that communicate with other elements within the assessment computing entity 100 via a bus, for example. As will be understood, the processing element 205 may be embodied in a number of different ways. For example, the processing element 205 may be embodied as one or more complex programmable logic devices (CPLDs), microprocessors, multi-core processors, coprocessing entities, application-specific instruction-set processors (ASIPs), microcontrollers, and/or controllers. Further, the processing element 205 may be embodied as one or more other processing devices or circuitry. The term circuitry may refer to an entirely hardware embodiment or a combination of hardware and computer program products. Thus, the processing element 205 may be embodied as integrated circuits, application specific integrated circuits (ASICs), field programmable gate arrays (FPGAs), programmable logic arrays (PLAs), hardware accelerators, other circuitry, and/or the like. As will therefore be understood, the processing element 205 may be configured for a particular use or configured to execute instructions stored in volatile or non-volatile media or otherwise accessible to the processing element 205. As such, whether configured by hardware or computer program products, or by a combination thereof, the processing element 205 may be capable of performing steps or operations according to embodiments of the present invention when configured accordingly.

In one embodiment, the assessment computing entity 100 may further include or be in communication with non-volatile media (also referred to as non-volatile storage, memory, memory storage, memory circuitry and/or similar terms used herein interchangeably). In one embodiment, the non-volatile storage or memory may include one or more non-volatile storage or memory media 210, including but not limited to hard disks, ROM, PROM, EPROM, EEPROM, flash memory, MMCs, SD memory cards, Memory Sticks, CBRAM, PRAM, FeRAM, NVRAM, MRAM, RRAM, SONOS, FJG RAM, Millipede memory, racetrack memory, and/or the like. As will be recognized, the non-volatile storage or memory media may store databases, database instances, database management systems, data, applications, programs, program modules, scripts, source code, object code, byte code, compiled code, interpreted code, machine code, executable instructions, and/or the like. The term database, database instance, database management system, and/or similar terms used herein interchangeably may refer to a collection of records or data that is stored in a computer-readable storage medium using one or more database models, such as a hierarchical database model, network model, relational model, entity-relationship model, object model, document model, semantic model, graph model, and/or the like.

In one embodiment, the assessment computing entity 100 may further include or be in communication with volatile media (also referred to as volatile storage, memory, memory storage, memory circuitry and/or similar terms used herein interchangeably). In one embodiment, the volatile storage or memory may also include one or more volatile storage or memory media 215, including but not limited to RAM, DRAM, SRAM, FPM DRAM, EDO DRAM, SDRAM, DDR SDRAM, DDR2 SDRAM, DDR3 SDRAM, RDRAM, TTRAM, T-RAM, Z-RAM, RIMM, DIMM, SIMM, VRAM, cache memory, register memory, and/or the like. As will be recognized, the volatile storage or memory media may be used to store at least portions of the databases, database instances, database management systems, data, applications, programs, program modules, scripts, source code, object code, byte code, compiled code, interpreted code, machine code, executable instructions, and/or the like being executed by, for example, the processing element 205. Thus, the databases, database instances, database management systems, data, applications, programs, program modules, scripts, source code, object code, byte code, compiled code, interpreted code, machine code, executable instructions, and/or the like may be used to control certain aspects of the operation of the assessment computing entity 100 with the assistance of the processing element 205 and operating system.

As indicated, in one embodiment, the assessment computing entity 100 may also include one or more communications interfaces 220 for communicating with various computing entities, such as by communicating data, content, information, and/or similar terms used herein interchangeably that can be transmitted, received, operated on, processed, displayed, stored, and/or the like. Such communication may be executed using a wired data transmission protocol, such as fiber distributed data interface (FDDI), digital subscriber line (DSL), Ethernet, asynchronous transfer mode (ATM), frame relay, data over cable service interface specification (DOCSIS), or any other wired transmission protocol. Similarly, the assessment computing entity 100 may be configured to communicate via wireless external communication networks using any of a variety of protocols, such as general packet radio service (GPRS), Universal Mobile Telecommunications System (UMTS), Code Division Multiple Access 2000 (CDMA2000), CDMA2000 1× (1×RTT), Wideband Code Division Multiple Access (WCDMA), Time Division-Synchronous Code Division Multiple Access (TD-SCDMA), Long Term Evolution (LTE), Evolved Universal Terrestrial Radio Access Network (E-UTRAN), Evolution-Data Optimized (EVDO), High Speed Packet Access (HSPA), High-Speed Downlink Packet Access (HSDPA), IEEE 802.11 (Wi-Fi), Wi-Fi Direct, 802.16 (WiMAX), ultra wideband (UWB), infrared (IR) protocols, near field communication (NFC) protocols, Wibree, Bluetooth protocols, wireless universal serial bus (USB) protocols, and/or any other wireless protocol.

Although not shown, the assessment computing entity 100 may include or be in communication with one or more input elements, such as a keyboard input, a mouse input, a touch screen/display input, motion input, movement input, audio input, pointing device input, joystick input, keypad input, and/or the like. The assessment computing entity 100 may also include or be in communication with one or more output elements (not shown), such as audio output, video output, screen/display output, motion output, movement output, and/or the like.

In various embodiments, the assessment computing entity 100 may further comprise a user interface for user interaction. In various embodiments, the user interface may comprise one or more input devices (e.g., soft or hard keyboard, joystick, mouse, touch screen device, microphone, and/or the like) for receiving user input and one or more output devices (e.g., speakers, display, and/or the like) for providing output to a user.

As will be appreciated, one or more of the assessment computing entity's 100 components may be located remotely from other assessment computing entity 100 components, such as in a distributed system. Furthermore, one or more of the components may be combined and additional components performing functions described herein may be included in the assessment computing entity 100. Thus, the assessment computing entity 100 can be adapted to accommodate a variety of needs and circumstances. As will be recognized, these architectures and descriptions are provided for exemplary purposes only and are not limiting to the various embodiments.

2. Exemplary User Computing Entity

Figure 3:
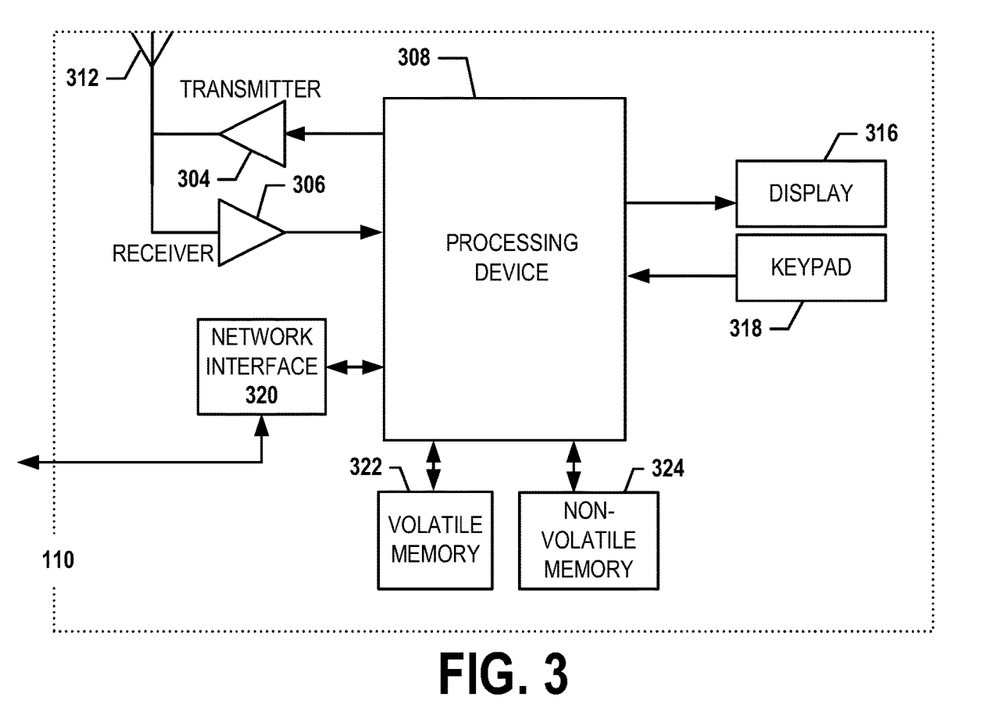
FIG. 3 is an exemplary schematic diagram of a user computing entity according to one embodiment of the present invention.

A user may be an individual, a family, a company, an organization, an entity, a department within an organization, a representative of an organization and/or person, and/or the like. In one example, users may be medical personnel, doctors, physician assistants, nurses, patients, and/or the like. For instance, a user may operate a user computing entity 110 that includes one or more components that are functionally similar to those of the assessment computing entity 100. FIG. 3 provides an illustrative schematic representative of a user computing entity 110 that can be used in conjunction with embodiments of the present invention. In general, the terms device, system, computing entity, entity, and/or similar words used herein interchangeably may refer to, for example, one or more computers, computing entities, desktops, mobile phones, tablets, phablets, notebooks, laptops, distributed systems, wearables, input terminals, servers or server networks, blades, gateways, switches, processing devices, processing entities, set-top boxes, relays, routers, network access points, base stations, the like, and/or any combination of devices or entities adapted to perform the functions, operations, and/or processes described herein. User computing entities 110 can be operated by various parties. As shown in FIG. 3, the user computing entity 110 can include an antenna 312, a transmitter 304 (e.g., radio), a receiver 306 (e.g., radio), and a processing element 308 (e.g., CPLDs, microprocessors, multi-core processors, coprocessing entities, ASIPs, microcontrollers, and/or controllers) that provides signals to and receives signals from the transmitter 304 and receiver 306, respectively.

The signals provided to and received from the transmitter 304 and the receiver 306, respectively, may include signaling information in accordance with air interface standards of applicable wireless systems. In this regard, the user computing entity 110 may be capable of operating with one or more air interface standards, communication protocols, modulation types, and access types. More particularly, the user computing entity 110 may operate in accordance with any of a number of wireless communication standards and protocols, such as those described above with regard to the assessment computing entity 100. In a particular embodiment, the user computing entity 110 may operate in accordance with multiple wireless communication standards and protocols, such as UMTS, CDMA2000, 1×RTT, WCDMA, TD-SCDMA, LTE, E-UTRAN, EVDO, HSPA, HSDPA, Wi-Fi, Wi-Fi Direct, WiMAX, UWB, IR, NFC, Bluetooth, USB, and/or the like. Similarly, the user computing entity 110 may operate in accordance with multiple wired communication standards and protocols, such as those described above with regard to the assessment computing entity 100 via a network interface 320.

Via these communication standards and protocols, the user computing entity 110 can communicate with various other entities using concepts such as Unstructured Supplementary Service Data (USSD), Short Message Service (SMS), Multimedia Messaging Service (MMS), Dual-Tone Multi-Frequency Signaling (DTMF), and/or Subscriber Identity Module Dialer (SIM dialer). The user computing entity 110 can also download changes, add-ons, and updates, for instance, to its firmware, software (e.g., including executable instructions, applications, program modules), and operating system.

According to one embodiment, the user computing entity 110 may include location determining aspects, devices, modules, functionalities, and/or similar words used herein interchangeably. For example, the user computing entity 110 may include outdoor positioning aspects, such as a location module adapted to acquire, for example, latitude, longitude, altitude, geocode, course, direction, heading, speed, universal time (UTC), date, and/or various other information/data. In one embodiment, the location module can acquire data, sometimes known as ephemeris data, by identifying the number of satellites in view and the relative positions of those satellites. The satellites may be a variety of different satellites, including Low Earth Orbit (LEO) satellite systems, Department of Defense (DOD) satellite systems, the European Union Galileo positioning systems, the Chinese Compass navigation systems, Indian Regional Navigational satellite systems, and/or the like. Alternatively, the location information can be determined by triangulating the user computing entity's 110 position in connection with a variety of other systems, including cellular towers, Wi-Fi access points, and/or the like. Similarly, the user computing entity 110 may include indoor positioning aspects, such as a location module adapted to acquire, for example, latitude, longitude, altitude, geocode, course, direction, heading, speed, time, date, and/or various other information/data. Some of the indoor systems may use various position or location technologies including RFID tags, indoor beacons or transmitters, Wi-Fi access points, cellular towers, nearby computing devices (e.g., smartphones, laptops) and/or the like. For instance, such technologies may include the iBeacons, Gimbal proximity beacons, Bluetooth Low Energy (BLE) transmitters, NFC transmitters, and/or the like. These indoor positioning aspects can be used in a variety of settings to determine the location of someone or something to within inches or centimeters.

The user computing entity 110 may also comprise a user interface (that can include a display 316 coupled to a processing element 308) and/or a user input interface (coupled to a processing element 308). For example, the user interface may be a user application, browser, user interface, and/or similar words used herein interchangeably executing on and/or accessible via the user computing entity 110 to interact with and/or cause display of information from the assessment computing entity 100, as described herein. The user input interface can comprise any of a number of devices or interfaces allowing the user computing entity 110 to receive data, such as a keypad 318 (hard or soft), a touch display, voice/speech or motion interfaces, or other input device. In embodiments including a keypad 318, the keypad 318 can include (or cause display of) the conventional numeric (0-9) and related keys (#, *), and other keys used for operating the user computing entity 110 and may include a full set of alphabetic keys or set of keys that may be activated to provide a full set of alphanumeric keys. In addition to providing input, the user input interface can be used, for example, to activate or deactivate certain functions, such as screen savers and/or sleep modes.

The user computing entity 110 can also include volatile storage or memory 322 and/or non-volatile storage or memory 324, which can be embedded and/or may be removable. For example, the non-volatile memory may be ROM, PROM, EPROM, EEPROM, flash memory, MMCs, SD memory cards, Memory Sticks, CBRAM, PRAM, FeRAM, NVRAM, MRAM, RRAM, SONOS, FJG RAM, Millipede memory, racetrack memory, and/or the like. The volatile memory may be RAM, DRAM, SRAM, FPM DRAM, EDO DRAM, SDRAM, DDR SDRAM, DDR2 SDRAM, DDR3 SDRAM, RDRAM, TTRAM, T-RAM, Z-RAM, RIMM, DIMM, SIMM, VRAM, cache memory, register memory, and/or the like. The volatile and non-volatile storage or memory can store databases, database instances, database management systems, data, applications, programs, program modules, scripts, source code, object code, byte code, compiled code, interpreted code, machine code, executable instructions, and/or the like to implement the functions of the user computing entity 110. As indicated, this may include a user application that is resident on the entity or accessible through a browser or other user interface for communicating with the assessment computing entity 100 and/or various other computing entities.

In another embodiment, the user computing entity 110 may include one or more components or functionality that are the same or similar to those of the assessment computing entity 100, as described in greater detail above. As will be recognized, these architectures and descriptions are provided for exemplary purposes only and are not limiting to the various embodiments.

3. Exemplary Imaging Machine

In various embodiments, an imaging machine 115 may be an imaging machine configured to capture and/or generate imaging information/data used to create a 2D, 3D, or 4D image of a portion of an individual's (e.g., patient, study participant, and/or the like) body. In various embodiments, the imaging machine 115 is configured for capturing and/or generating imaging information/data through at least one of the various imaging techniques and/or processes such as, for example, fluoroscopy, magnetic resonance imaging (MRI), photoacoustic imaging, positron emission tomography (PET), projection radiography, computed axial tomography (CT scan), and ultrasound. In an example embodiment, the imaging machine 115 is an MRI machine configured for capturing and/or generating image information/data of an individual's (e.g., patient, study participant, and/or the like) brain. In an example embodiment, the imaging machine 115 is an MRI machine configured for dMRI imaging.

In an example embodiment, the imaging machine 115 may be operated by the assessment computing entity 100 and/or other controller computing entity. In an example embodiment, the imaging machine and/or controller computing entity thereof may communicate with the assessment computing entity 100 directly and/or via one or more wired and/or wireless networks 105. For example, the imaging machine 115 may be configured to provide imaging information/data to the assessment computing entity 100 for analysis, storage, and/or the like. In another example, the assessment computing entity 100 and/or other controller computing entity may provide instructions to the imaging machine 115 regarding beginning an imaging session, pausing an imaging session, aborting an imaging session, ending an imaging session, and/or the like.

III. Exemplary System Operation

According to various embodiments, the assessment computing entity 100 may be configured to analyze one or more instances of imaging information/data. In an example embodiment, an instance of imaging information/data may comprise the imaging information/data of one imaging session and/or a portion of one imaging session, for one individual (e.g., patient, study participant, and/or the like). The term "image" is used generically to refer to a variety of images that can be generated from various imaging techniques and processes. The imaging techniques and processes may include, for instance, diffusion MRI. As indicated, the images can be of a human body or one or more parts of the human body (e.g., a patient and/or study participant's brain), but the images can also be of other organisms or objects. A "volume of images" or "volume" refers to a sequence of images that can be spatially related and assembled into a rectilinear block representing a dimensional region of an individual's (e.g., patient, study participant, and/or the like) anatomy. In various embodiments, the imaging information/data captured and analyzed comprises dMRI data. Although the following is described in the context of MRI scans, embodiments of the present invention are not limited to this context.

In an example embodiment, one or more instances of imaging information/data may be captured and/or generated for an individual (e.g., patient, study participant, and/or the like), wherein an instance of imaging information/data may comprise a dMRI image. For example, dMRI imaging information/data may be analyzed using a bi-tensor analysis to determine the amount and/or fraction of free-water present within one or more areas of an individual's (e.g., patient, study participant, and/or the like) brain. In an example embodiment, two or more instances of imaging data/information, and/or the analysis thereof, corresponding to the same individual (e.g., patient, study participant, and/or the like) may be compared, analyzed as a set, and/or the like. For example, the two or more instances of imaging data/information may be captured and/or generated at different times (e.g., separated by a week, a month, two months, six months, a year, two years, four years, and/or the like). Such analysis may be used to determine a progression or lack of progression of a disease, such as Parkinson's or other parkinsonian disease; measure the efficacy of a drug and/or other therapy at treating, slowing, and/or halting the progression of a disease, such as Parkinson's or other parkinsonian disease; determine a risk level, score, and/or the like for the individual (e.g., patient, study participant, and/or the like) of developing a disease or condition, such as Parkinson's or other parkinsonian disease; diagnose early stages of a disease, such as Parkinson's or other parkinsonian disease, before the primary diagnostic symptoms (e.g., movement and/or motor symptoms) become evident; and/or the like. For example, various embodiments may be provide for determining a parkinsonian state for an individual. Additionally, various embodiments are configured to identify a treatment for an individual for treating a parkinsonian disease. In various embodiments, the imaging information/data is analyzed using an automated normalization pipeline that is configured to automatically identify one or more regions of the individual's brain within the imaging information/data.

Determining an Individual's Parkinsonian State

Figure 4:
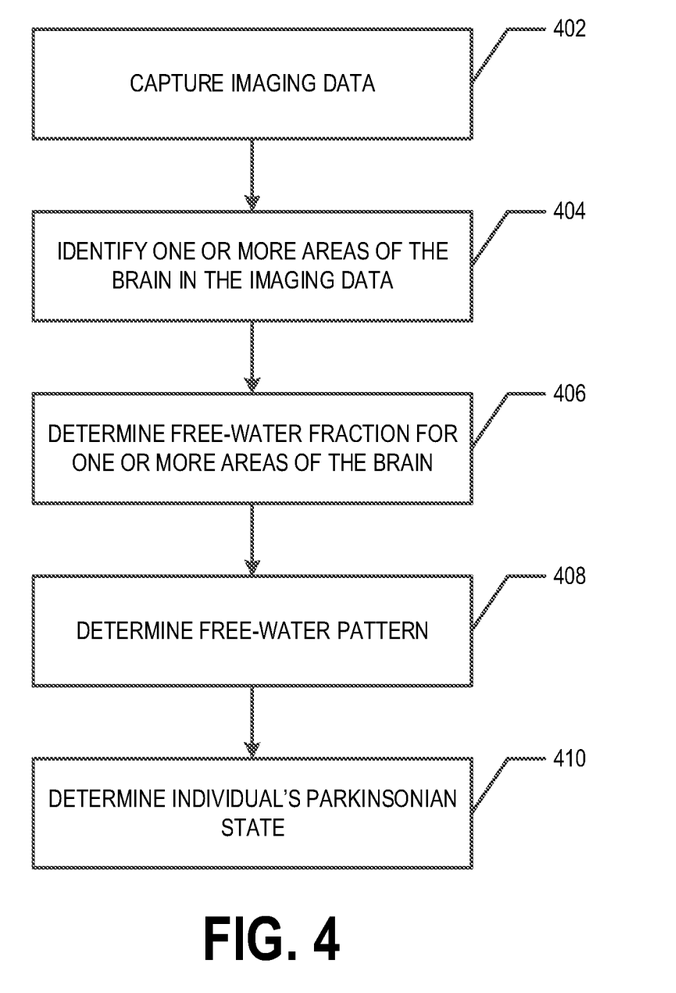
FIG. 4 provides a flowchart illustrating example processes, procedures, and/or operations for determining an individual's parkinsonian state.

FIG. 4 provides a flowchart of various processes, procedures, operations, and/or the like that may be completed to determine an individual's parkinsonian state, identify a free-water pattern for an individual's brain, and/or the like. In various embodiments, the individual may be an individual patient. In various embodiments, the individual may be a study participant for a drug study or other treatment study.

Starting at block 402, imaging information/data is captured. For example, the assessment computing entity 100 may receive from or cause an imaging device 115 to capture imaging information/data of an individual. For example, an imaging technician may provide the individual with instructions and position the individual within and/or in the proximity of the imaging device 115. The imaging technician may then provide input (e.g., via a user input device) to the assessment computing entity 100 to trigger the assessment computing entity 100 to cause, instruct, trigger, and/or the like the imaging device 115 to capture imaging information/data of the individual. The assessment computing entity 100 may receive the captured imaging information/data from the imaging device 115 and store the imaging information/data and corresponding metadata in memory 210, 215. For example, the metadata may include the individual's name or an individual identifier, a date and/or time stamp, information/data identifying the imaging device 115, and/or the like. In an example embodiment, the imaging information/data captured may comprise dMRI data and/or the like. In various embodiments, the imaging information/data may comprise one or more images of an individual's brain and/or a portion thereof.

At block 404, one or more portions of imaging information/data corresponding to one or more areas of the brain are identified. For example, the one or more areas of the brain that are identified may be referred to as regions of interest. In an example embodiment, the regions of interest may comprise one or more of the anterior substantia nigra, posterior substantia nigra, putamen, caudate nucleus, globus pallidus, subthalamic nucleus, middle cerebellar peduncle, superior cerebellar peduncle, cerebellar lobule VI, inferior vermis, pedunculopontine nucleus, hippocampus, and/or the like. For example, the assessment computing entity 100 may receive user input (e.g., via an input device) that identify portions of imaging information/data corresponding to regions of interest. For example, the assessment computing entity 100 may display one or more images corresponding to the imaging information/data to a skilled technician via an output device (e.g., display of the assessment computing entity 100, display 316 of a user computing entity 110, and/or the like). The assessment computing entity 100 may then receive an indication of user input (e.g., received via an input device of the assessment computing entity 100 or of the user computing entity 110) identifying one or more portions of the one or more images that correspond to particular areas of the individual's brain. For example, the skilled technician may provide input to the input device of the assessment computing entity 100 or user computing entity 110 identifying In an example embodiment, the portions of imaging information/data corresponding to the regions of interest are identified by the assessment computing entity 100. For example, the assessment computing entity 100 may use a trained neural network, deep net, or other model that was trained using machine learning to identify one or more portions of the imaging information/data corresponding to one or more areas of the brain. For example, the assessment computing entity 100 may use a normalization pipeline, one or more templates, and/or the like for identifying one or more portions of the imaging information/data corresponding to one or more areas of the brain such as the regions of interest.

In various embodiments, the imaging information/data may be pre-processed before being provided (e.g., displayed) for skilled technician identification of the regions of interest and/or automated identification of the regions of interest. For example, in an example embodiment, the imaging information/data may be preprocessed using FMRIB Software Library (FSL, http://www.fmrib.ox.ac.uk/fsl/) and custom UNIX shell scripts. For example, each scan of the imaging information/data was corrected for signal distortions due to eddy currents and head motion. For example, gradient directions may be rotated in response to the eddy current corrections, and portions of the imaging information/data corresponding to non-brain tissue may be removed from the imaging information/data. In example embodiment, we use custom algorithms to quantify b0 and corrected fractional anisotropy images from the imaging information/data. In various embodiments, the b0 image is the diffusion image without gradients applied with diffusion weighting and is similar to a standard T2 weighted MRI. Free-water images and free-water-corrected diffusion tensor images may be calculated using custom algorithms in MATLAB or another mathematical analysis software based on the imaging information/data. In an example embodiment, a bi-tensor model is used to calculate the signal attenuation as the sum of attenuations arising from two compartments: one that models free-water and a tissue compartment. The free-water-corrected tensor images were also used to calculate free-water corrected fraction anisotropy maps ($FA_T$). Data preprocessing may be used to generate fractional anisotropy, b0, free-water, $FA_T$ and/or other images from and/or based on the imaging data, in various embodiments. In an example embodiment, the fractional anisotropy and b0 images were multiplied together to maximize contrast in the midbrain and the cortex, and will hereafter be referred to as the FA*b0 image. In an example embodiment, the portions of imaging information/data corresponding to the regions of interest are identified in the b0 image in subject space. For example, an image provided for skilled technician identification of one or more regions of interest may be a b0 image in subject space.

In some example embodiments, FLIRT/FNIRT in FSL software and/or rigid alignment and Symmetric Normalization (SyN) in Advanced Normalization Tools (ANTs) software may be used to provide a normalization pipeline for processing imaging information/data and/or identifying one or more portions of imaging information/data corresponding to regions of interest. In some example embodiments, FLIRT/FNIRT in FSL software and/or rigid alignment and Symmetric Normalization (SyN) in Advanced Normalization Tools (ANTs) software may be used to generate one or more templates used to identify one or more portions of the imaging information/data corresponding to one or more regions of interest and/or use one more templates to identify portions of the imaging information/data corresponding to regions of interest. In an example embodiment, at least one of the templates corresponds to and/or is generated based on mean b0, fractional anisotropy, or b0*FA images. In an example embodiment, the imaging information/data is analyzed and/or the templates are in Montreal Neurological Institute (MNI) space. Processing through this pipeline is an automated computer driven procedure that can than link to cloud based architecture or laptops computing devices, or the like (e.g., a user computing entity 110).

In various embodiments, to transform the subject space imagine data (e.g., the imaging information/data received from the imaging device 115 and/or the pre-processed imaging data) to MNI space, a series of nonlinear and linear registrations may be used. In various embodiments, prior to nonlinear registration, a linear registration (e.g., FLIRT in FSL and a rigid transformation in ANTs) may be applied to the imaging information/data. In an example embodiment, three linear registrations may be completed in FSL, ANTs, and/or the like to get subject-space images to MNI space. In an example embodiment, the three linear registrations comprise (1) b0 registration to a mean 100 Human Connectome Project (HCP) b0 template, (2) fractional anisotropy registration to a mean HCP fractional anisotropy template, and (3) FA*b0 registration to a mean HCP FA*b0 template. Linear registrations were followed with nonlinear warping (e.g., FNIRT in FSL and SyN in ANTs). In an example embodiment, three different nonlinear warps may be performed for FSL, ANTs, and/or the like. For example, the three different nonlinear warps may comprise (1) b0 warping to a mean HCP b0 template, (2) fractional anisotropy warping to a mean HCP fractional anisotropy template, and (3) FA*b0 warping to a mean HCP FA*b0 template. In an example embodiment, default settings may be used for all registration and warping.

At block 406, a free-water fraction is determined for one or more areas of the brain based on the imaging information/data. For example, the free-water fraction for one or more regions of interest may be determined based on the portions of imaging information/data corresponding to the respective regions of interest. For example, the assessment computing entity 100 may determine the free-water fraction for a region of interest based on the portion of the imaging information/data identified as corresponding to the region of interest. In various embodiments, the free-water fraction is derived from imaging information/data captured via dMRI scan. Various methods for deriving the free-water fraction for a region of interest may be used in various embodiments.

At block 408, a free-water pattern for the individual may be determined. In an example embodiment, the free-water pattern may comprise the free-water fraction determined for each of a one or more regions of interest. For instance, the assessment computing entity 100 may determine a free-water pattern for the individual based on the imaging information/data. In an example embodiment, the free-water pattern may be a list of one or more regions of interest and/or other areas of the individuals brain and the determined free-water fraction corresponding to the one or more regions of interest and/or other areas of the individual's brain, a relative measure of the free-water fraction corresponding to the one or more regions of interest and/or other areas of the individual's brain (e.g., relative to one or more other regions of interest and/or other areas of the individual's brain, relative to a normal brain template, and/or the like), and/or the like. In an example embodiment, the free-water pattern may be an image or brain map indicating the determined free-water fraction corresponding to the one or more regions of interest and/or other areas of the individual's brain, a relative measure of the free-water fraction corresponding to the one or more regions of interest and/or other areas of the individual's brain (e.g., relative to one or more other regions of interest and/or other areas of the individual's brain, relative to a normal brain template, and/or the like), and/or the like. In various embodiments, the free-water pattern may be an absolute or relative description of the free-water fraction in two or more regions of interest and/or other areas of the individual's brain.

At block 410, the free-water pattern may be used to determine the individual's parkinsonian status. For example, the assessment computing entity 100 may determine the individual's parkinsonian status based on the free-water pattern. In various embodiments, the free-water pattern may be used to determine if the individual has a parkinsonian disease, if the individual is at risk of developing a parkinsonian disease, and/or the like. Further, the free-water pattern may be used to determine a type of parkinsonian disease (e.g., Parkinson's disease (PD), multiple system atrophy (MSA), and progressive supranuclear palsy (PSP), atypical parkinsonism, cortical basal syndrome, and/or the like) that the individual has or is at risk of developing. In various embodiments, the individual's parkinsonian state may be determined by matching the individual's free-water pattern to a most similar free-water pattern template, by determining if the individual's free-water pattern satisfies one or more one-dimensional, two-dimensional, or three-dimensional predetermined threshold requirements, and/or the like. In various embodiments, the free-water pattern templates and/or predetermined threshold requirements may be empirically derived, determined, and/or the like. In various embodiments, an individual's parkinsonians state may be that the individual does not and/or is unlikely to have a parkinsonian disease, is at risk of developing a parkinsonian disease, has an early stage parkinsonian disease, has a middle stage parkinsonian disease, has a late stage parkinsonian disease, has a particular parkinsonian disease (e.g., PD, MSA, PSP, atypical parkinsonism, cortical basal syndrome, and/or the like), and/or the like.

After determining the individual's parkinsonian state, the individual's parkinsonian state may be provided to a skilled technician (e.g., laboratory technician, physician, physician assistant, nurse, and/or the like). For example, the assessment computing entity 100 may provide the determined individual's state via an output device (e.g., display), communications interface 220, and/or the like. For example, the user computing entity 110 may receive a message comprising the determined individual's parkinsonian state and provide the individual's parkinsonian state via display 316, and/or other output device of the user computing entity 110.

In various embodiments, the determination of an individual's parkinsonian state may be used for research (e.g., in a medical research study, a drug or other treatment study, and/or the like), to determine a course of treatment for the individual (e.g., a set of one or more prescriptions, physical therapy, occupational therapy, and/or other therapy), and/or the like. In an example embodiment, the assessment computing entity 100 may provide a suggested course of treatment for the individual. In various embodiments, the course of treatment may be determined by one or more physicians and/or other healthcare providers.

Determining a Treatment Efficacy

Figure 5:
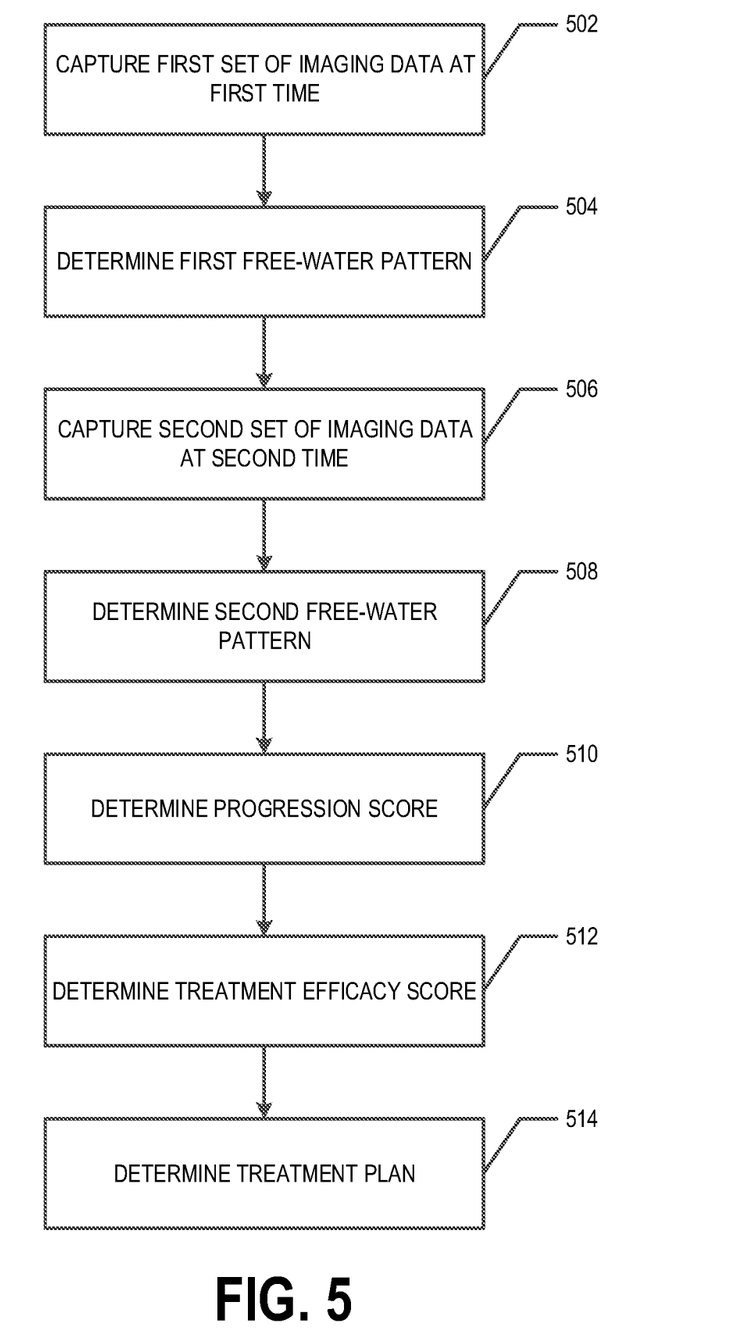
FIG. 5 provides a flowchart illustrating example processes, procedures, and/or operations for treating an individual having a parkinsonian disease.

FIG. 5 provides a flowchart illustrating various processes, procedures, operations, and/or the like for determining a disease progression score, determining a treatment efficacy, determining a course of treatment, and/or the like for an individual having and/or at risk of developing parkinsonian disease.

Starting at block 502, a first set of imaging information/data is captured at a first date and/or time. For example, the assessment computing entity 100 may cause an imaging device 115 to capture a first set of imaging information/data of an individual. For example, an imaging technician may provide the individual with instructions and position the individual within and/or in the proximity of the imaging device 115. The imaging technician may then provide input (e.g., via a user input device) to the assessment computing entity 100 to trigger the assessment computing entity 100 to cause, instruct, trigger, and/or the like the imaging device 115 to capture the first set of imaging information/data of the individual. The assessment computing entity 100 may receive the captured first set of imaging information/data from the imaging device 115 and store the first set of imaging information/data and corresponding metadata in memory 210, 215. For example, the metadata may include the individual's name or an individual identifier, a date and/or time stamp indicating a first date and/or time at which first set of imaging information/data was captured, information/data identifying the imaging device 115, and/or the like. In an example embodiment, the first set of imaging information/data captured may comprise dMRI data, and/or the like. In various embodiments, the first set of imaging information/data may comprise one or more images of an individual's brain and/or a portion thereof.

At block 504, a first free-water pattern is determined for the individual at the first date and/or time. In various embodiments, the first set of imaging data is pre-processed to remove any motion artifacts and/or distortions prior to the determining of the first free-water pattern. In an example embodiment, the pre-processing of the first set of imaging data may be performed via an automated pipeline (e.g., performed by the assessment computing entity 100, and/or the like). For example, the assessment computing entity 100 may determine a first free-water pattern for the individual at the first date and/or time. For example, a technique similar to that described for block 404-408 above may be used to determine a first free-water pattern based on the first set of imaging information/data. For example, one or more portions of the first set of imaging information/data corresponding to one or more areas of the individual's brain may be identified. For example, one or more portions of the first set of imaging information/data corresponding to regions of interest may be identified. Free-water fractions for one or more regions of interest and/or other areas of the individual's brain may be determined based on the corresponding portions of the first set of imaging information/data. The determined free-water fractions and/or the first set of imaging information/data may then be used to derive and/or determine the first free-water pattern for the individual at the first date and/or time.

Starting at block 506, a second set of imaging information/data is captured at a second date and/or time. In various embodiments the second set of imaging information/data is captured at a second date and/or time that is after the first date and/or time. In an example embodiment, the second set of imaging information/data is captured at a second date and/or time that is at least a minimum time window after the first date and/or time. In various embodiments, the minimum time window may be a week, a month, a three months, half a year, one year, more than one year, and/or the like. In an example embodiment, the minimum time window may be predetermined and/or may be determined based on the first free-water pattern.

In an example embodiment, the assessment computing entity 100 may cause an imaging device 115 to capture a second set of imaging information/data of an individual at the second date and/or time. For example, an imaging technician may provide the individual with instructions and position the individual within and/or in the proximity of the imaging device 115. The imaging technician may then provide input (e.g., via a user input device) to the assessment computing entity 100 to trigger the assessment computing entity 100 to cause, instruct, trigger, and/or the like the imaging device 115 to capture the second set of imaging information/data of the individual. The assessment computing entity 100 may receive the captured second set of imaging information/data from the imaging device 115 and store the second set of imaging information/data and corresponding metadata in memory 210, 215. For example, the metadata may include the individual's name or an individual identifier, a date and/or time stamp indicating a second date and/or time at which second set of imaging information/data was captured, information/data identifying the imaging device 115, and/or the like. In an example embodiment, the second set of imaging information/data captured may comprise dMRI data, and/or the like. In various embodiments, the second set of imaging information/data may comprise one or more images of an individual's brain and/or a portion thereof.

At block 508, a second free-water pattern is determined for the individual at the second date and/or time. In various embodiments, the second set of imaging data is pre-processed to remove any motion artifacts and/or distortions prior to the determining of the second free-water pattern. In an example embodiment, the pre-processing of the second set of imaging data may be performed via an automated pipeline (e.g., performed by the assessment computing entity 100, and/or the like). For example, the assessment computing entity 100 may determine a second free-water pattern for the individual at the first date and/or time. For example, a technique similar to that described for blocks 404-408 above may be used to determine a second free-water pattern based on the second set of imaging information/data. For example, one or more portions of the second set of imaging information/data corresponding to one or more areas of the individual's brain may be identified. For example, one or more portions of the second set of imaging information/data corresponding to regions of interest may be identified. Free-water fractions for one or more regions of interest and/or other areas of the individual's brain may be determined based on the corresponding portions of the second set of imaging information/data. The determined free-water fractions and/or the second set of imaging information/data may then be used to derive and/or determine the second free-water pattern for the individual at the second date and/or time.

At block 510, a progression score is determined. For example, the assessment computing entity 100 may determine a progression score for the individual based on the first and second free-water pattern. For example, the progression score may be determined by fitting a first template to the first free-water pattern and/or identifying one or more first threshold requirements satisfied by the first free-water pattern and fitting a second template to the second free-water pattern and/or identifying one or more second threshold requirements satisfied by the second free-water pattern. The first and second templates and/or first and second threshold requirements may each be associated with a disease stage and the differences between the disease stages associated with the first and second templates and/or the first and second threshold requirements may be taken as the progression score. In another example embodiment, the differences between the first free-water pattern and the second free-water pattern may be determined to generate a difference free-water pattern. The difference free-water pattern may then be fit to a difference template and/or one or more difference threshold requirements satisfied by the difference free-water pattern may be identified. The difference template and/or difference threshold requirements may each be associated with a disease progression. Thus, progression score may be determined based on the fitted difference template and/or identified one or more difference threshold requirements. In various embodiments, the first, second, and/or difference threshold requirements may be one-dimensional, two-dimensional, or three-dimensional threshold requirements.

In an example embodiment, the assessment computing entity 100 may store in memory 210, 215 and/or access a sequence of templates, threshold requirements, difference templates, and/or difference threshold requirements to determine which template, threshold requirements, difference template, and/or difference threshold requirements provide the best fit and/or are satisfied by the first free-water pattern, second free-water pattern, and/or difference free-water pattern. As shown by the inventor, changes in the free-water pattern of an individual is not linear with disease progression for parkinsonian diseases. In particular, the free-water pattern of an individual changes more rapidly at earlier stages of the disease than at later stages of the disease. Thus, the sequence of templates, threshold requirements, difference templates, and/or difference threshold requirements may include a larger number of templates, threshold requirements, difference templates, and/or difference threshold requirements corresponding to earlier stages of one or more parkinsonian diseases.

In another example embodiment, a first parkinsonian state is determined based on the first free-water pattern and a second parkinsonian state is determined based on the second free-water pattern. The progression score may be determined based on the number of states and/or distance between the first parkinsonian state and the second parkinsonian state. In another example embodiment, the progression score may provide a likelihood that the individual having the first parkinsonian state at the first date and/or time would have the second parkinsonian state and the second date and/or time based on the natural progression of the parkinsonian disease.

At block 512, a treatment efficacy score is determined. For example, the assessment computing entity 100 may determine a treatment efficacy score. As described above, a treatment comprise one or more drugs, pharmaceuticals, and/or prescriptions, physical therapy, occupational therapy, and/or the like. For example, the treatment efficacy score may provide an indication of how well a treatment or treatment plan has prevented and/or reversed the natural progression of the parkinsonian disease. In an example embodiment, the treatment efficacy score is determined based on the determined progression score, the amount of time and/or time window between the first date and/or time and the second date and/or time, the portion of the amount of time between the first date and/or time and the second date and/or time for which the individual has been undergoing the treatment, and/or the like. For example, if the natural progression of the parkinsonian disease of an average individual having a first parkinsonian state at the first time is a third parkinsonian state at the second date and/or time, and it is determined that the individual had a first parkinsonian state at the first date and/or time and a second parkinsonian state at the second date and/or time, the second parkinsonian state being intermediate between the first parkinsonian state and the third parkinsonian state, the treatment efficacy score may indicate a "distance" between the second parkinsonian state and the third parkinsonian state. The "distance" may be a time difference (e.g., the amount of time between an average individual usually has the second parkinsonian state and the average individual has the third parkinsonian state in accordance with natural disease progression), a rate difference (e.g., a difference in the rate of progression of the disease with respect to natural disease progression in an average individual), a percent difference (e.g., a percentage difference between the expected third parkinsonian state and the determined second parkinsonian state), and/or the like.

In various embodiments, the progression score, treatment efficacy score, and/or a second parkinsonian state determined for the individual based on the second free-water pattern may be provided. For example, the individual's progression score, treatment efficacy score, and/or second parkinsonian state may be provided to a skilled technician (e.g., laboratory technician, physician, physician assistant, nurse, and/or the like). For example, the assessment computing entity 100 may provide the determined individual's progression score, treatment efficacy score, and/or second parkinsonian state via an output device (e.g., display), communications interface 220, and/or the like. For example, the user computing entity 110 may receive a message comprising the determined individual's progression score, treatment efficacy score, and/or second parkinsonian state and provide the individual's parkinsonian state via display 316, and/or other output device of the user computing entity 110. In various embodiments, the individual's progression score, treatment efficacy score, second parkinsonian state, and/or the like may be stored in a treatment and/or drug study database stored in memory 210, 215, and/or the like.

At block 514, a treatment plan may be determined for the individual. For example, the treatment plan may be determined based on the second parkinsonian state, the treatment efficacy score, progression score, and/or the like. In an example embodiment, the assessment computing entity 100 may provide a suggested course of treatment for the individual. In various embodiments, the course of treatment may be determined by one or more physicians and/or other healthcare providers. In various embodiments, the determination of an individual's progression score, treatment efficacy score, and/or second parkinsonian state may be used for research (e.g., in a medical research study such as, for example, a medical research study that includes evaluation of one or more pharmaceutical drug trial or other treatment and/or therapy).

Advantages

Various embodiments of the present invention provide significant technical advantages and address technical challenges of treating parkinsonian disease, evaluating treatment efficacy in treating parkinsonian disease, and/or the like. For example, various embodiments provide for a normalized, repeatable, and consistent manner for identifying various areas of an individual's brain from imaging data for determining a free-water pattern for an individual's brain. The current procedures provide a brain derived template, pipeline for registering to the template, procedures for quantifying free-water and other diffusion patterns, and automated procedures for assessing parkinsonian state. Additionally, various embodiments of the present invention provide for treatment of parkinsonian disease using a non-invasive biomarker. Various embodiments of the present invention provide a treatment efficacy score that may be used to determine the efficacy of a treatment such that the treatment may be evaluated. For example, the evaluation may be for an individual or for a treatment and/or drug study.

IV. Conclusion

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

The invention claimed is:

1. A method of determining a treatment efficacy score for a treatment for treating a parkinsonian disease in an individual, the method comprising:
receiving, at a computing entity, a first set of imaging information/data associated with a dMRI scan of an individual's brain and associated with a first time;
receiving, at the computing entity, a second set of imaging information/data associated with a dMRI scan of the individual's brain and associated with a second time, wherein the individual undergoes a treatment for a time period, the time period comprising at least a portion of the time between the first time and the second time;
determining, at the computing entity, an expected change between the first time and the second time based on a natural progression of the parkinsonian disease;
analyzing, at the computing entity, at least a portion of the first set of imaging information/data to determine a first free-water pattern;
analyzing, at the computing entity, at least a portion of the second set of imaging information/data to determine a second free-water pattern;
based on the first free-water pattern and the second free-water pattern, determining, at the computing entity, a disease progression score; and
based on the disease progression score and the expected change between the first time and the second time, determining, at the computing entity, a treatment efficacy for treating the individual with the treatment.

2. The method of claim 1, further comprising, based on at least one of (a) the disease progression score, (b) the treatment efficacy score, (c) the first free-water pattern or (d) the second free-water pattern, determining a treatment plan for the individual.

3. The method of claim 1, wherein the one or more areas of the individual's brain comprise one or more of the anterior anterior substantia nigra, posterior substantia nigra, putamen, caudate nucleus, globus pallidus, subthalamic nucleus, middle cerebellar peduncle, superior cerebellar peduncle, cerebellar lobule VI, inferior vermis, pedunculopontine nucleus, or hippocampus.

4. The method of claim 1, wherein the expected change is determined based on a control group of individuals.

5. The method of claim 1, wherein the expected change does not progress linearly with time for at least one area of the individual's brain.

6. The method of claim 1, wherein the expected change comprises a change in a free-water fraction in the posterior substantia nigra that is steeper at earlier stages of the parkinsonian disease compared to at later stages of the parkinsonian disease.

7. The method of claim 1, wherein the individual is a participant in a drug or other therapy study and the treatment efficacy score indicates the degree to which the drug or other therapy has slowed the progression of the parkinsonian disease the individual has.

8. An apparatus comprising at least one processor, a communications interface configured for communicating via at least one network, and at least one memory storing computer program code, the at least one memory and the computer program code configured to, with the processor, cause the apparatus to at least:
receive a first set of imaging information/data associated with a dMRI scan of an individual's brain and associated with a first time;
receive a second set of imaging information/data associated with a dMRI scan of the individual's brain and associated with a second time, wherein the individual undergoes a treatment for a time period, the time period comprising at least a portion of the time between the first time and the second time;
determine an expected change between the first time and the second time based on a natural progression of the parkinsonian disease;
analyze at least a portion of the first set of imaging information/data to determine a first free-water pattern;
analyze at least a portion of the second set of imaging information/data to determine a second free-water pattern;
based on the first free-water pattern and the second free-water pattern, determine a disease progression score; and
based on the disease progression score and the expected change between the first time and the second time, determine a treatment efficacy for treating the individual with the treatment.

9. The apparatus of claim 8, wherein a treatment plan is determined for the individual based at least in part on at least one of (a) the disease progression score, (b) the treatment efficacy score, (c) the first free-water pattern or (d) the second free-water pattern.

10. The apparatus of claim 8, wherein the one or more areas of the individual's brain comprise one or more of the anterior substantia nigra, posterior substantia nigra, putamen, caudate nucleus, globus pallidus, subthalamic nucleus, middle cerebellar peduncle, superior cerebellar peduncle, cerebellar lobule VI, inferior vermis, pedunculopontine nucleus, or hippocampus.

11. The apparatus of claim 8, wherein the expected change is determined based on a control group of individuals.

12. The apparatus of claim 8, wherein the expected change does not progress linearly with time for at least one area of the individual's brain.

13. The apparatus of claim 8, wherein the expected change comprises a change in a free-water fraction in the posterior substantia nigra that is steeper at earlier stages of the parkinsonian disease compared to at later stages of the parkinsonian disease.

14. The apparatus of claim 8, wherein the individual is a participant in a drug or other therapy study and the treatment efficacy score indicates the degree to which the drug or other therapy has slowed the progression of the parkinsonian disease the individual has.

15. A computer program product comprising at least one non-transitory computer-readable storage medium having computer-readable program code portions stored therein, the computer-readable program code portions comprising executable portions configured, when executed by a processor of an apparatus, to cause the apparatus to:
receive a first set of imaging information/data associated with a dMRI scan of an individual's brain and associated with a first time;
receive a second set of imaging information/data associated with a dMRI scan of the individual's brain and associated with a second time, wherein the individual undergoes a treatment for a time period, the time period comprising at least a portion of the time between the first time and the second time;
determine an expected change between the first time and the second time based on a natural progression of the parkinsonian disease;
analyze at least a portion of the first set of imaging information/data to determine a first free-water pattern;

analyze at least a portion of the second set of imaging information/data to determine a second free-water pattern;

based on the first free-water pattern and the second free-water pattern, determine a disease progression score; and based on the disease progression score and the expected change between the first time and the second time, determine a treatment efficacy for treating the individual with the treatment.

16. The computer program product of claim 15, wherein a treatment plan is determined for the individual based at least in part on at least one of (a) the disease progression score, (b) the treatment efficacy score, (c) the first free-water pattern or (d) the second free-water pattern.

17. The computer program product of claim 15, wherein the one or more areas of the individual's brain comprise one or more of the anterior substantia nigra, posterior substantia nigra, putamen, caudate nucleus, globus pallidus, subthalamic nucleus, middle cerebellar peduncle, superior cerebellar peduncle, cerebellar lobule VI, inferior vermis, pedunculopontine nucleus, or hippocampus.

18. The computer program product of claim 15, wherein the expected change is determined based on a control group of individuals.

19. The computer program product of claim 15, wherein the expected change does not progress linearly with time for at least one area of the individual's brain.

20. The computer program product of claim 15, wherein the expected change comprises a change in a free-water fraction in the posterior substantia nigra that is steeper at earlier stages of the parkinsonian disease compared to at later stages of the parkinsonian disease.

* * * * *